United States Patent
Jiang

(10) Patent No.: US 6,177,094 B1
(45) Date of Patent: Jan. 23, 2001

(54) BIOABSORBABLE BLENDS AND COATING COMPOSITION CONTAINING SAME

(75) Inventor: Ying Jiang, Raleigh, NC (US)

(73) Assignee: United States Surgical Corporation, Norwalk, CT (US)

(*) Notice: Under 35 U.S.C. 154(b), the term of this patent shall be extended for 0 days.

(21) Appl. No.: 09/243,123

(22) Filed: Jan. 29, 1999

Related U.S. Application Data

(60) Provisional application No. 60/083,754, filed on Apr. 30, 1998.

(51) Int. Cl.[7] .............................. A61F 2/02; A61K 47/30; A61B 17/04
(52) U.S. Cl. .................. 424/426; 514/772.3; 606/228; 606/230
(58) Field of Search .................. 424/426; 514/772.3; 606/228, 230

(56) References Cited

U.S. PATENT DOCUMENTS

| | | | |
|---|---|---|---|
| 3,169,945 | 2/1965 | Hostettler et al. | 260/78.3 |
| 3,531,561 | 9/1970 | Trehu | 606/231 |
| 3,867,190 | 2/1975 | Schmitt et al. | 606/231 |
| 3,912,692 | 10/1975 | Casey et al. | 528/354 |
| 3,942,532 | 3/1976 | Hunter et al. | 128/335.5 |
| 4,027,676 | 6/1977 | Mattei | 128/335.5 |
| 4,043,344 | 8/1977 | Landi et al. | 606/230 |
| 4,047,533 | 9/1977 | Perciaccante | 606/230 |
| 4,080,969 | 3/1978 | Casey et al. | 606/231 |
| 4,105,034 | 8/1978 | Shalaby et al. | 606/230 |
| 4,185,637 | 1/1980 | Mattei | 128/335.5 |
| 4,201,216 | 5/1980 | Mattei | 606/230 |
| 4,470,416 | 9/1984 | Kafrawy et al. | 128/335.5 |
| 4,605,730 | 8/1986 | Shalaby et al. | 528/357 |
| 4,624,256 | 11/1986 | Messier et al. | 128/333.5 |
| 4,643,191 | 2/1987 | Bezwada et al. | 128/333.5 |
| 4,649,920 | 3/1987 | Rhum | 606/237 |
| 4,653,497 | 3/1987 | Bezweda et al. | 128/333.5 |
| 4,700,704 | 10/1987 | Jamiolkowski et al. | 128/333.5 |
| 4,705,820 | 11/1987 | Wang et al. | 524/381 |
| 4,711,241 | 12/1987 | Lehmann | 128/335.5 |
| 4,716,203 | 12/1987 | Casey et al. | 606/230 |
| 4,744,365 | 5/1988 | Kaplan et al. | 606/230 |
| 4,788,979 | 12/1988 | Jarrett et al. | 128/335.5 |
| 4,791,929 | 12/1988 | Jarrett et al. | 128/335.5 |
| 4,857,602 | 8/1989 | Casey et al. | 606/230 |
| 4,994,074 | 2/1991 | Bezwada et al. | 606/230 |
| 5,076,807 | 12/1991 | Bezwada et al. | 606/230 |
| 5,080,665 | 1/1992 | Jarrett et al. | 606/230 |
| 5,085,629 | 2/1992 | Goldberg et al. | 604/8 |
| 5,100,433 | 3/1992 | Bezwada et al. | 606/230 |
| 5,116,932 | 5/1992 | Fujiwa | 528/80 |
| 5,123,912 | 6/1992 | Kaplan et al. | 606/230 |
| 5,210,108 | 5/1993 | Spinu et al. | 521/182 |
| 5,225,521 | 7/1993 | Spinu | 528/354 |
| 5,278,202 | 1/1994 | Dunn et al. | 523/113 |
| 5,312,437 | 5/1994 | Hermes et al. | 606/230 |
| 5,352,515 | 10/1994 | Jarrett et al. | 428/357 |
| 5,399,666 | 3/1995 | Ford | 528/354 |
| 5,442,033 | * 8/1995 | Bezwada | 528/354 |
| 5,543,218 | 8/1996 | Bennett et al. | 428/375 |

FOREIGN PATENT DOCUMENTS

| | | |
|---|---|---|
| 0117538 | 9/1984 | (EP) . |
| 0239775 | 10/1987 | (EP) . |
| WO 8404311 | 11/1984 | (WO) . |

OTHER PUBLICATIONS

Grijpma et al., 'Star–shaped polyactide–containing block copolymers', Makromol Chem., Rapid Commun. vol. 14, pp. 155–161 (1993).

* cited by examiner

*Primary Examiner*—Carlos A. Azpuru

(57) ABSTRACT

A bioabsorbable blend is provided which comprises the reaction product of 1) a bioabsorbable copolymer obtained by polymerizing a major amount of epsilon-caprolactone and a minor amount of at least one other copolymerizable monomer in the presence of a polyhydric alcohol initiator and 2) the reaction product obtained by mixing polyalkylene glycol and a coplymer of glycolide/lactide copolymer. The blend has many uses, including that of a coating for a surgical suture.

18 Claims, No Drawings

BIOABSORBABLE BLENDS AND COATING COMPOSITION CONTAINING SAME

This application claims benefit to U.S. provisional application Ser. No. 60/083,754 filed Apr. 30, 1998.

BACKGROUND OF THE INVENTION

A blend of bioabsorbable copolymers is disclosed. More particularly, a blend of 1) a bioabsorbable copolymer obtained by polymerizing a major amount of epsilon-caprolactone and a minor amount of at least one other copolymerizable monomer in the presence of a polyhydric alcohol initiator and 2) the reaction product obtained by mixing polyalkylene glycol and a coplymer of glycolide/lactide copolymer is disclosed.

It is well known in the art that surgical sutures may be coated to enhance certain physical characteristics of the suture, such as the ease of a sliding a knot into place on the suture, commonly referred to as knot repositioning or knot run down. Suitable surgical suture coatings must exhibit good knot run down without being so lubricious as to sacrifice knot security.

U.S. Pat. No. 5,312,437 discloses an absorbable suture coating composition comprising the product obtained by reacting a mixture of poly(oxypropylene)glycol and a coplymer of lactide/glycolide copolymer.

U.S. Pat. No. 5,425,949 discloses a bioabsorbable copolymer obtained by polymerizing a major amount of epsilon-caprolactone and a minor amount of at least one other copolymerizable monomer in the presence of a polyhydric alcohol initiator. The copolymer can be used as a suture coating.

Notwithstanding the suitable suture coatings described above, it would be advantageous to provide another bioabsorbable suture coating such that when applied to multifilament bioabsorbable sutures, the physical characteristics of the multifilament sutures are even more enhanced.

SUMMARY OF THE INVENTION

A blend is provided which comprises the reaction product of 1) a bioabsorbable copolymer obtained by polymerizing a major amount of epsilon-caprolactone and a minor amount of at least one other copolymerizable monomer in the presence of a polyhydric alcohol initiator and 2) the reaction product obtained by mixing polyalkylene glycol and a coplymer of glycolide/lactide copolymer.

DESCRIPTION OF THE PREFERRED EMBODIMENTS

The bioabsorbable blend may be prepared by conventional methods well known in the art. Preferably, about 70 to about 90 percent by weight epilon-caprolactone containing copolymer is mixed with about 10 to about 30 percent by weight of the polyalkylene glycol containing glycol mixture at about 150° C. and stirred for about 4 hours. More preferrebly, about 80 percent by weight epilon-caprolactone containing copolymer is mixed with about 20 percent by weight of the polyalkylene glycol containing glycol mixture at about 150° C. and stirred for about 4 hours.

Suitable epsilon-caprolactone containing coplymers may be polymerized by conventional polymerization techniques that are well known and disclosed in the prior art can be utilized in preparing the bioabsorbable copolymer of the present invention. The bioabsorbable copolymer is obtained by polymerizing a major amount of epsilon-caprolactone and a minor amount of at least one other copolymerizable monomer or mixture of such monomers in the presence of a polyhydric alcohol initiator. The polymerization of these monomers contemplates all of the various types of monomer addition, i.e., simultaneous, sequential, simultaneous followed by sequential, sequential followed by simultaneous, etc.

Suitable monomers which can be copolymerized with epsilon-caprolactone include glycolide, lactide, p-dioxanone and trimethylene carbonate.

Suitable polyhydric alcohol initiators include glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxyethyl)ethylenediamine, N,N,N',N'-tetrakis(2-hydroxypropyl)ethylenediamine, dipentaerythritol, allitol, dulcitol, glucitol, altritol, iditol, sorbitol, mannitol, inositol, and the like. The use of a polyhydric alcohol initiator, i.e., an alcohol possessing three or more hydroxyl groups, provides a copolymer having a branched, or "star", configuration. The branched structure of the bioabsorbable copolymer herein exerts a characteristic influence on its bioabsorption behavior making it useful, among other applications, as a component in a surgical suture coating material.

Suitable epsilon caprolactone containing copolymers can contain from about 70 to about 98, and preferably from about 80 to about 95, weight percent epsilon-caprolactone-derived units, the balance of the copolymer being derived from the other copolymerizable monomer(s). The inherent viscosity of the copolymer generally ranges from about 0.10 to about 0.60, and preferably from about 0.20 to about 0.50, dl/g when measured in chloroform at a concentration of 0.2500 g/dl at 30° C. The polyhydric alcohol initiator is generally employed in small amounts, e.g., from about 0.5 to about 5, and preferably from about 0.1 to about 2, weight percent of the total monomer mixture.

The poly(alkylene)glycol containing composition with which the epsilon-caprolactone copolymer is blended preferrably is obtained by reacting a mixture of poly(alkylene) glycol with a lactide/glycolide copolymer in the presence or absence of an initiator.

Preferably the poly(alkylene)glycol is poly(ethylene) glycol or poly(propylene)glycol, with poly(propylene) glycol being most preferred. Suitable poly(propylene) glycols have a molecular weight ranging from about 400 to about 6000 and more preferrably from about 1000 to about 4000. Suitable poly(propylene)glycols include Pluracol, Voranol, Poly G, Polylite, Thanol, and Niax, commercially available from BASF-Wyandotte, Dow Chemical Company, Olin, Reichhold, Texaco and Union Carbide, respectively.

Suitable lactide/glycolide copolymers include from about 65 to about 90 mole percent lactide and from about 10 to about 35 mole percent glycolide and about 0 to about 5 mole percent of other bioabsorbable monomers copolymerizable therewith, such as epsilon-caprolactone, dioxanone, and trimethylene carbonate, etc. Preferably the gylcolide/lactide copolymers have from about 85 to about 70 mole percent lactide and about 15 to about 30 mole percent glycolide, with 82 mole percent lactide and 18 mole percent glycolide being most preferred. Suitable lactide/glycolide copolymers possess a glass transistion temperature of at least about 54° C. when measured by differential scanning calorimetry at 20° C./min and an inherent viscosity of at least about 0.9 when measured in chloroform at a concentration of 0.25 g/dl.

The poly(propylene)glycol containing composition is prepared by reacting poly(propylene)glycol with lactide/ glycolide copolymers, generally in the presence of an esterification catalyst such as stannous chloride, stannous octoate, etc., and, optionally, an initiator. Suitable initiators include glycols such as ethylene glycol, propylene glycol, diethylene glycol and dipropylene glycol, with diethylene glycol being preferred. The weight ratio of poly(propylene)glycol to lactide/glycolide copolymer can range from about 4:1 to about 1:4 and preferrably from about 2:1 to about 1:2, respectively. Typically, the reaction is carried out in an inert atmosphere, e.g., nitrogen, at temperatures ranging from about 125° C. to about 200° C. and preferrably from about 150° C. to about 160° C. Suitable poly(propylene)glycol containing compositions, possess and inherent viscosity of at least about 0.9 and more preferrably below about 0.5, when measured in chloroform at a concentration of 0.25 g/dl.

The bioabsorbable blend is non-toxic and physiologically inert. Depending on its particular physical and bioabsorption properties (to a large extent influenced by the nature of the initiators and monomers from which it is prepared), the bioabsorbable blend herein can be used in the fabrication in whole or in part of a variety of implantable medical devices and prostheses, e.g., clips, staples, sutures, suture coatings, etc. Applied to a suture, a coating composition containing the bioabsorbable blend results in a suture having suitable lubricity, knot tiedown and knot security characteristics.

The bioabsorbable blend herein can be applied to a suture by any suitable process, e.g., passing the suture through a solution of the copolymer, e.g., in acetone, methylene chloride, etc., past a brush or other coating solution applicator, or past one or more spray nozzles dispensing the suture coating solution. The suture wetted with the coating solution is subsequently passed through or held in a drying oven for a time and at a temperature sufficient to vaporize and drive off the solvent. If desired, the suture coating composition can optionally contain additional components, e.g., dyes, antibiotics, antiseptics, growth factors, anti-inflammatory agents, etc.

While the coating composition herein can be applied to any type of suture, it is essentially intended for application to a braided suture such as that disclosed in U.S. Pat. No. 5,019,093. The amount of coating composition applied to a braided suture will vary depending upon the structure of the suture, e.g., the number of filaments, tightness of braid or twist, the size of the suture and its composition. Suitable coating levels range from about 1 to about 10 percent by weight of the suture.

In order that those skilled in the art may be better able to practice the blends herein, the following example is given as an illustration of the preparation of the blend disclosed herein. It should be noted that the invention is not limited to the specific details embodied in the example.

EXAMPLE 1

In a container under nitrogen flow, 100 grams of copolymer comprising about 90 weight percent epsilon-caprolactone and about 10 percent by weight glycolide and 100 grams of a composition comprising about 50 percent by weight polypropylene glycol and about 50 percent by weight of a copolymer containing about 18 percent glycolide and about 82 percent by weight lactide are dissolved in 1000 grams of methylene chloride. The reaction product is then isolated, comminuted, and treated to remove residual reactants using known techniques.

What is claimed is:

1. A bioabsorbable blend comprising the reaction product of component A and component B wherein:

component A comprises a copolymer obtained by polymerizing a major amount of epsilon-caprolactone and a minor amount of at least one other copolymerizable monomer in the presence of polyhydric alcohol as initiator; and component B comprises a composition comprising the product obtained by reacting a mixture of poly (propylene)glycol and lactide glycolide copolymer.

2. The blend of claim 1 wherein the other copolymerizable monomer is selected from the group consisting of glycolide, lactide, p-dioxanone and trimethylene carbonate.

3. The blend of claim 1 wherein the polyhydric alcohol initiator is selected from the group consisting of glycerol, trimethylolpropane, 1,2,4-butanetriol, 1,2,6-hexanetriol, triethanolamine, triisopropanolamine, erythritol, threitol, pentaerythritol, ribitol, arabinitol, xylitol, N,N,N',N'-tetrakis (2-hydroxy-ethyl)ethylenediamine, N,N,N',N'-tetrakis(2-hydroxypropyl)ethylenediamine, dipentaerythritol, allitol, dulcitol, glucitol, altritol, iditol, sorbitol, mannitol and inositol.

4. The blend of claim 1 wherein the copolymer of component A comprises from about 70 to about 98 weight percent epsilon-caprolactone-derived units, the balance of the copolymer being derived from the other copolymerizable monomer(s).

5. The blend of claim 1 wherein the copolymer of component A comprises from about 80 to about 95 weight percent epsilon-caprolactone derived units, the balance of the copolymer being derived from the other copolymerizable monomer(s).

6. The blend of claim 1 wherein the polyhydric alcohol is employed in an amount of from about 0.5 to about 5 weight percent of the total monomer mixture.

7. The blend of claim 1 wherein the polyhydric alcohol initiator is employed in an amount of from about 0.1 to about 2 weight percent of the total monomer mixture.

8. The blend of claim 1 wherein the poly(alkylene)glycol is seleceted from the group consisting of poly(ethylene) glycol and poly(propylene)glycol.

9. The blend of claim 1 wherein the poly(alkylene)glycol has a molecular weight of about 400 to about 6000.

10. The blend of claim 1 wherein the lactide/glycolide copolymer is prepared from L-lactide.

11. The blend of claim 1 wherein the lactide/glycolide copolymer comprises from about 90 to about 65 mole percent lactide and from about 10 to about 35 mole percent glycolide.

12. The blend of claim 1 wherein the weight ratio of poly(propylene)glycol to lactide glycolide copolymer in component B is from about 4:1 to about 1:4.

13. The blend of claim 1 wherein the weight ratio of poly(propylene)glycol to lactide glycolide copolymer in component B is from about 2:1 to about 1:2.

14. The blend of claim 1 comprising about 30 to about 70 weight percent of component A and 70 to about 30 weight percent of component B.

15. A medical device fabricated in whole or in part from the blend of claim 1.

16. A surgical suture coated with a coating composition comprising the blend of claim 1.

17. The surgical suture of claim 16 which is a bioabsorbable braided suture.

18. The suture of claim 16 wherein the coating composition is applied to a suture at a level of 1 to about 10 weight percent of the entire coated suture.

\* \* \* \* \*